US00PP26773P3

(12) United States Plant Patent
Bacon

(10) Patent No.: US PP26,773 P3
(45) Date of Patent: May 31, 2016

(54) PEACH TREE NAMED 'SUPECHTWENTYONE'

(50) Latin Name: *Prunus persica*
Varietal Denomination: Supechtwentyone

(71) Applicant: Sun World International, LLC, Bakersfield, CA (US)

(72) Inventor: Terry A. Bacon, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 106 days.

(21) Appl. No.: 14/121,383

(22) Filed: Aug. 28, 2014

(65) Prior Publication Data
US 2016/0066487 P1 Mar. 3, 2016

(51) Int. Cl.
*A01H 5/00* (2006.01)

(52) U.S. Cl.
USPC ..... Plt./197

(58) Field of Classification Search
USPC ..... Plt./197
See application file for complete search history.

*Primary Examiner* — Annette Para
(74) *Attorney, Agent, or Firm* — Knobbe, Martens, Olson & Bear, LLP

(57) ABSTRACT

A new and distinct peach tree variety, *Prunus persica,* cv. 'Supechtwentyone' is characterized by its large size fruit, later ripening and flesh that becomes red with maturity.

1 Drawing Sheet

Latin name of the genus and species claimed: *Prunus persica.*

Variety denomination: 'SUPECHTWENTYONE'.

BACKGROUND AND SUMMARY OF THE INVENTION

This invention relates to the discovery and asexual propagation of a new and distinct variety of peach, *Prunus persica* cv. 'Supechtwentyone'. The new variety was first selected on May 29, 2010 by Terry Bacon as breeder number 'PE1194'. The new variety was first evaluated by Terry Bacon near Wasco, Calif. in Kern County. The variety 'Supechtwentyone' was originated by hybridization.

The new variety 'Supechtwentyone' is characterized by its large size fruit, later ripening and flesh that becomes red with maturity.

The seed parent is 'PE226' (unpatented variety), and the pollen parent is 'Supechseventeen' (U.S. Plant Pat. No. 22,588). The parent varieties were first crossed in February 2006, with the date of first sowing being February 2007, and the date of first flowering being February 2008. The new peach variety 'Supechtwentyone' was first asexually propagated by Terry Bacon near Wasco, Kern County, Calif. in January 2012 by grafting.

The new variety 'Supechtwentyone' is distinguished from its seed parent, 'PE226' (unpatented variety), in that the new variety ripens about five days later than 'PE226' (unpatented variety). The fruit of the new variety 'Supechtwentyone' is larger at 72 mm compared to 68 mm for the fruit of its seed parent 'PE226'. Additionally, the flesh of the new variety 'Supechtwentyone' becomes red as it ripens while the flesh of its seed parent 'PE226' remains yellow.

The new variety 'Supechtwentyone' is distinguished from its pollen parent, 'Supechseventeen' (U.S. Plant Pat. No. 22,588), in that fruit maturity begins about eleven days later for the new variety than for 'Supechseventeen' (U.S. Plant Pat. No. 22,588).

The new variety 'Supechtwentyone' ripens at a similar time in the season as 'Rich May' (U.S. Plant Pat. No. 7,432) and 'Burpeachone (U.S. Plant Pat. No. 12,156). However, the fruit diameter of the new variety 'Supechtwentyone' is larger at 72 mm compared to that of 'Rich May' (U.S. Plant Pat. No. 7,432) at 66 mm. The flesh of the fruit of the new variety 'Supechtwentyone' becomes red as it matures while the flesh of the fruit of 'Rich May' and 'Burpeachone' remains uniformly yellow.

The new variety 'Supechtwentyone' has been shown to maintain its distinguishing characteristics through successive asexual propagations by, for example, budding and grafting.

BRIEF DESCRIPTION OF THE DRAWING

The accompanying color photographic illustration (FIG. 1) shows typical specimens of the foliage and fruit of the present new peach variety 'Supechtwentyone'. The illustration shows the upper and lower surface of the leaves and exterior and sectional views of the fruit. The photographic illustration was taken shortly after the fruit was picked and the colors are as nearly true as is reasonably possible in a color representation of this type.

DETAILED DESCRIPTION OF THE PREFERRED EMBODIMENT

Throughout this specification, color names beginning with a small letter signify that the name of that color, as used in common speech is aptly descriptive. Color names beginning with a capital letter designate values based upon The R.H.S. Colour Chart published by The Royal Horticultural Society, London, England, 1986.

Unless otherwise noted, the descriptive matter which follows pertains to 3 year old 'Supechtwentyone' trees on Nemaguard (unpatented) rootstock, grown in the vicinity of Wasco, Kern County, Calif., during 2014, and is believed to apply to plants of the variety grown under similar conditions of soil and climate elsewhere.

TREE

General:

*Size*.—Medium. Normal for most peach varieties. Reaches a height of approximately 3 meters with normal pruning.

*Spread*.—Normal for most peach varieties. Approximately 3 meters with normal pruning.

*Vigor*.—Medium; growth of about 1.8 to about 2 meters in height during the first growing season.

*Growth*.—Semi-upright.

*Productivity*.—Productive. Fruit set is usually two or more times the desired amount for marketable size fruit; thinning and spacing of fruit is necessary.

*Form*.—Vase formed.

*Bearer*.—Regular.

*Fertility*.—Self-fertile.

*Canopy density*.—Dense.

*Hardiness*.—Hardy in all fruit growing areas of California; winter chilling requirement is approximately 250 hours at or below 7.2° C.

*Disease resistance/susceptibility*.—No specific testing for relative plant disease resistance/susceptibility has been undertaken. Under close observation in Kern County, Calif., no particular plant/fruit disease resistance/susceptibility has been observed.

Trunk: (Measurements at approximately 30 cm above soil line.).

*Diameter*.—Approximately 17 cm.

*Texture*.—Medium shaggy, increases with age of tree.

*Trunk color*.—Outer bark about Light Greyed-green 197D to about Dark Greyed-green 197A; inner bark about Dark Greyed-orange 177A to about Medium Greyed-orange 174B.

Branches: (Measurements at approximately 90 cm above soil line.).

*Size*.—Approximately 9 cm.

*Texture*.—Medium shaggy; increasing with tree age.

*Color*.—About Light Greyed-green 197D to about Medium Greyed-orange 166D.

*Number of lenticels*.—Medium.

*Lenticels density*.—Approximately 2-4 per $cm^2$.

*Lenticels color*.—About Medium Greyed-orange 166D.

*Lenticels size*.—Medium.

*Lenticels length*.—Approximately 3 mm.

*Lenticels width*.—Approximately 1.5 mm.

Flowering shoots: (Data taken in June at midpoint of current-season growth.).

*Size*.—Average diameter approximately 5 mm.

*Color*.—Topside: About Medium Yellow-green 146C. Underside: About Medium Yellow-green 146C.

*Internode length*.—Medium; approximately 3 cm. Midway on flowering shoot.

*Flowering shoot lenticels*.—Sparse. Color: About Medium Yellow-green 148B. Diameter: Approximately 0.3 mm.

*Flowering shoot leaf buds*.—Shape: Elliptic to conical. Width: Approximately 3 mm. Length: Approximately 4 mm. Color: About Medium Greyed-green 197C.

*Flowering shoot flower buds*.—Shape: Conical. Width: Approximately 25 mm. Length: Approximately 4 mm. Color: About Medium Greyed-green 197C. Number of buds per node: Usually 2.

*Flower bud hardiness*.—Medium-hardy.

*Density of buds*.—Medium.

*Internode length*.—Medium, about 3 cm, midway on flowering shoots.

*Flower bud distribution*.—Generally isolated in groups of 2 on one year old shoots.

*Ratio of wood (leaf) buds to flowering shoots*.—1/2.

FOLIAGE

Leaves: (Data taken in June on fully expanded leaf at midpoint of current-season growth).

*Size*.—Medium.

*Average length*.—Medium; approximately 12-14 cm.

*Average width*.—Medium; approximately 3-4 cm.

*Thickness*.—Medium.

*Color*.—Upper Surface: About Dark Green 137A. Lower Surface: About Medium Green 137C.

*Form*.—Lanceolate.

*Tip*.—Cuspidate.

*Base*.—V-shaped.

*Margin*.—Crenate.

*Venation*.—Pinnately veined.

*Vein color*.—About Light Green 138C.

*Surface texture*.—Smooth.

*Leaf blade (ratio of length to width)*.—Medium; about 4/1.

*Shape in the cross section*.—Concave.

*Angle at apex*.—Medium.

*Profile*.—Up folded.

*Leaf blade tip*.—Curved downwardly.

*Angle of tip*.—Acute.

*Undulation of margin*.—Slight.

Petiole:

*Average length*.—Medium; approximately 10 mm.

*Average diameter*.—Approximately 2 mm.

*Color*.—About Light Green 138C.

Stipules:

*Number/leaf bud*.—Approximately 2.

*Typical length*.—Approximately 7 mm.

*Color*.—About Dark Greyed-orange 176A when dry.

*Persistence*.—Falls off.

Leaf glands:

*Form*.—Renaform.

*Average number*.—Between about 2 and 6; usually 2.

*Position*.—On petiole mainly and base of leaf, alternate.

*Average size*.—Medium; approximately 1 by 2 mm.

*Color*.—About Medium Yellow-green 144B.

FLOWERS

General:

*Flower blooming period*.—First Bloom: Approximately February 4. Full Bloom: Approximately February 11.

*Time of bloom*.—Early.

*Location of first bloom*.—Lower third of the canopy.

*Location of full bloom*.—Throughout the canopy, with fully opened flowers.

*Duration of bloom*.—Medium; approximately 10 days.

*Type of bloom*.—Non-showy.

*Diameter of fully opened flower*.—Medium, approximately 37 mm.

*Flower aroma*.—Slight aroma.

*Shape*.—Non-showy.

Peduncle:
*Length*.—Medium; approximately 4 mm.
*Diameter*.—Slender; approximately 1.5 mm.
*Color*.—About Medium Yellow-green 144A.
*Pubescence*.—Absent.
Petals:
*Number*.—5.
*Arrangement*.—Free.
*Length*.—Approximately 13 mm.
*Diameter*.—Approximately 7 mm.
*Shape*.—Elliptic.
*Apex shape*.—Rounded.
*Base shape*.—Narrows, cuneate.
*Color*.—Inner Surface: About Light Red-purple 62B, becoming darker over time. Outer Surface: About Light Red-purple 62B, becoming darker over time.
*Surface texture*.—Smooth.
*Margins*.—Slightly undulating.
*Frequency of flowers with double petals*.—Few to none.
*Petal size*.—Medium.
*Claw*.—Absent.
*Margin waviness*.—Weak.
*Base angle*.—Medium.
*Division of upper margin*.—Entire.
*Pubescence of inner surface*.—Absent.
*Pubescence of outer surface*.—Absent.
Sepals:
*Number*.—5.
*Length*.—Approximately 5 mm.
*Diameter*.—Approximately 3 mm.
*Shape*.—Triangular.
*Color*.—About Medium Red-purple 64B outside surface.
*Surface texture*.—Smooth.
*Margins*.—Entire.
*Positioning*.—Touching petals when opened.
*Pubescence of inner surface*.—Absent.
*Pubescence of outer surface*.—Absent.
*Frequency of flowers with double sepals*.—None.
Stamens:
*Number*.—Many; usually 37-47.
*Average length*.—Approximately 12 mm.
*Filament color*.—About Light Red-purple 62C, darkening to Medium Red-purple 64B, as flower ages.
*Anther color*.—About Medium Red-purple 61B.
*Flower pollen color*.—About Dark Yellow-orange 22A when dried.
*Position*.—Perigynous.
Pistil:
*Number*.—Usually one.
*Average length*.—Approximately 18 mm.
*Ovary diameter*.—Approximately 1.5 mm.
*Pubescence*.—None.
*Stigma extension in comparison to anthers*.—Usually with and above.
*Frequency of supplementary pistils*.—Few.
Receptacle:
*Depth*.—Medium.
*Pubescence of inner surface* (*at pink bud stage*).—Absent.
*Pubescence of outer surface*.—Absent.
Ovary:
*Pubescence*.—Slight.
*Density of hairs*.—Dense.

FRUIT

General: (Description taken at firm-ripe on mature tree managed to obtain maximum quality).
*Harvest*.—
*Date of first pick*.—Approximately May 13.
*Date of last pick*.—Approximately May 23.
*Maturity when described*.—Firm-mature.
*Season ripening*.—Early.
*Position of maximum diameter*.—Towards the middle.
*Symmetry about the suture*.—Somewhat symmetric.
*Size*.—Length (Stem End to Apex): Approximately 68 mm. Diameter in Line with Suture Plane: Approximately 72 mm.
*Diameter perpendicular to suture plane*.—Approximately 72 mm.
*Average weight*.—Approximately 205 gm.
*Form*.—Viewed from Apex: Rounded, nearly symmetrical. Viewed from Side, Facing Suture: Rounded, nearly symmetrical. Viewed from Side, Perpendicular to Suture: Rounded, nearly symmetrical.
*Apex shape*.—Rounded.
*Apex base*.—Rounded.
Fruit stem cavity:
*Shape*.—Rounded.
*Depth*.—Medium; approximately 0.8 cm.
*Breadth*.—Approximately 1.5 cm.
*Width*.—Medium.
Fruit stem:
*Length*.—Medium, approximately 9 mm.
*Diameter*.—Approximately 2.5 mm.
*Color*.—About Medium Greyed-orange 164B.
*Adherence to stone*.—Medium.
Fruit skin:
*Thickness*.—Medium.
*Adherence to flesh*.—Strong.
*Surface texture*.—Medium.
*Pubescence*.—Slight.
*Bloom*.—Absent.
*Ground color*.—About Medium Yellow 12A when mature.
*Overcolor*.—About Medium Red 53B to Light Red 53D.
*Taste*.—Neutral.
*Reticulation*.—Absent.
*Roughness*.—Absent.
*Tenacity*.—Tenacious to flesh.
*Tendency to crack*.—None, in wet season.
Flesh:
*Ripens*.—Evenly.
*Texture*.—Firm, non-melting.
*Fibers*.—Few.
*Flavor*.—Mildly sweet with medium-low acidity.
*Brix*.—Approximately 13°.
*Juice*.—Moderate.
*Aroma*.—Slight.
*Color*.—When ripe, about Dark Yellow 17A near the stone, and about Medium Red 42A developing around perimeter to middle of the flesh.
*Anthocyanin color of flesh*.—About Medium Red 42A strongly expressed at firm-mature.
*Anthocyanin color around stone*.—Absent or weakly expressed when firm-mature.

*Amygdalin*.—Wanting.
*Acidity*.—Medium-low.
*Sugar content*.—Medium, 13 brix.
*Eating quality*.—Good.
*Stone/flesh ratio*.—About 1/4.
*Firmness*.—Firm.

Shape of pistil point: Rounded.

Pit cavity size:

*Length*.—Approximately 30 mm.
*Diameter in line with suture plane*.—Approximately 28 mm.
*Diameter perpendicular to suture plane*.—Approximately 25 mm.
*Color*.—About Dark Yellow 17A.

Fruit use: Fresh market.

Fruit shipping and keeping quality: Good.

Suture line: Inconspicuous.

Stone:

*Stone freeness*.—Semi-free over the entire surface.
*Degree of adherence to flesh*.—Strong.
*Stone size*.—Medium. Size compared to Fruit: Medium. Length: Medium, approximately 28 mm. Diameter in Line with Suture plane: Approximately 22 mm. Diameter Perpendicular to Suture Plane: Approximately 18 mm. Width of Stalk End: Medium; approximately 3 mm. Angle of Stalk end: Right angle. Hilum: Oval, nearly symmetrical.
*Stone form*.—Viewed from Side: Oval. Viewed from Ventral Side: Oval.
*Stone shape*.—Base shape: Nearly straight. Apex shape: Pointed. Hilum: Oval.
*Stone surface*.—Pitted throughout.
*Stone halves*.—Nearly symmetric.
*Stone ridges*.—Rounded continuous.
*Stone outgrowing keel*.—Partially developed.
*Stone tendency to split*.—Slight in wet season.
*Stone color*.—About Medium Greyed-orange 166C when dried.
*Position of maximum*.—Toward middle.
*Sides*.—Nearly equal.
*Pits*.—Angular.
*Fibers*.—Short.
*Ventrical edge*.—Medium.
*Dorsal edge*.—Narrow grooves, interrupted.

What is claimed is:

1. A new and distinct peach tree as herein described and illustrated.

* * * * *

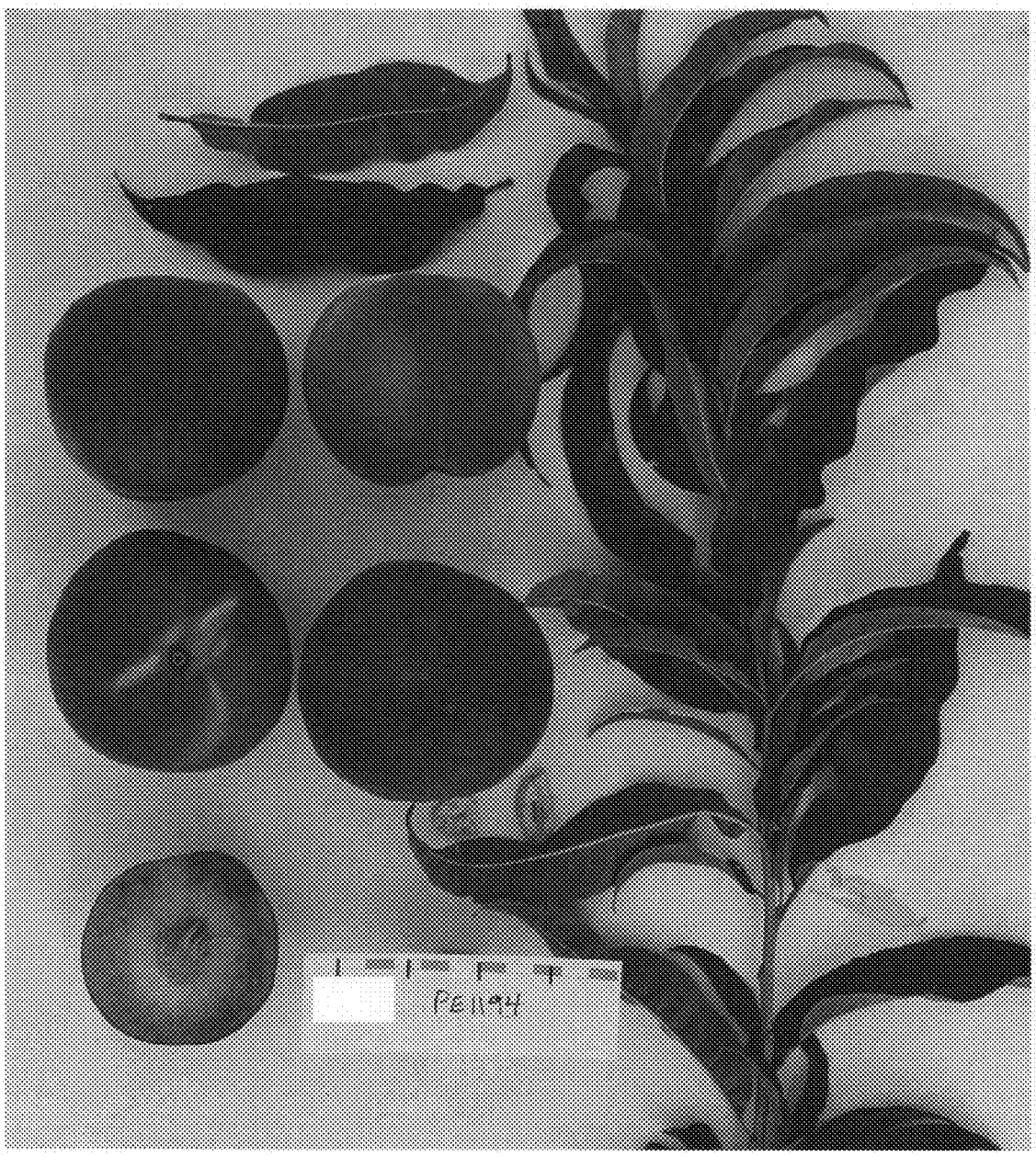
PE1194